United States Patent
Maschke

(10) Patent No.: US 8,359,086 B2
(45) Date of Patent: *Jan. 22, 2013

(54) DEVICE FOR APPLYING AND MONITORING MEDICAL ATHERECTOMY

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1582 days.

This patent is subject to a terminal disclaimer.

(21) Appl. No.: 11/062,304

(22) Filed: Feb. 18, 2005

(65) Prior Publication Data

US 2005/0187571 A1   Aug. 25, 2005

(30) Foreign Application Priority Data

Feb. 20, 2004   (DE) .......................... 10 2004 008 371

(51) Int. Cl.
*A61B 17/00*   (2006.01)

(52) U.S. Cl. ................ 600/427; 604/22; 606/159

(58) Field of Classification Search .......... 600/427, 600/481, 562, 564; 606/159; 604/22
See application file for complete search history.

(56) References Cited

U.S. PATENT DOCUMENTS

| | | | |
|---|---|---|---|
| 5,193,546 A | 3/1993 | Shaknovich | |
| 5,366,464 A * | 11/1994 | Belknap | 606/159 |
| 5,634,464 A | 6/1997 | Jang et al. | |
| 5,662,671 A * | 9/1997 | Barbut et al. | 606/170 |
| 5,865,748 A | 2/1999 | Co et al. | |
| 5,895,402 A | 4/1999 | Hundertmark et al. | |
| 5,957,941 A * | 9/1999 | Ream | 606/159 |
| 6,010,449 A * | 1/2000 | Selmon et al. | 600/117 |
| 6,258,052 B1 | 7/2001 | Milo | |
| 6,485,413 B1 * | 11/2002 | Boppart et al. | 600/160 |
| 2002/0019644 A1 * | 2/2002 | Hastings et al. | 606/159 |
| 2002/0077647 A1 | 6/2002 | Snow et al. | |
| 2003/0120295 A1 * | 6/2003 | Simpson et al. | 606/159 |
| 2003/0125757 A1 | 7/2003 | Patel et al. | |
| 2004/0186368 A1 * | 9/2004 | Ramzipoor et al. | 600/407 |
| 2005/0203553 A1 * | 9/2005 | Maschke | 606/159 |

FOREIGN PATENT DOCUMENTS

| | | |
|---|---|---|
| DE | 198 27 460 A1 | 12/1998 |
| WO | WO 00/07641 | 2/2000 |

* cited by examiner

*Primary Examiner* — Parikha Mehta

(57) ABSTRACT

Device for carrying out and monitoring an atherectomy, with which a cutting knife driven in a rotating manner by an external unit and set back to project into an opening in the tip of the catheter can be pressed onto the artery wall by means of an inflatable balloon arranged on the side of the catheter casing opposite the window opening, an atherectomy catheter being connected to an OCT catheter to form an integrated unit.

7 Claims, 1 Drawing Sheet

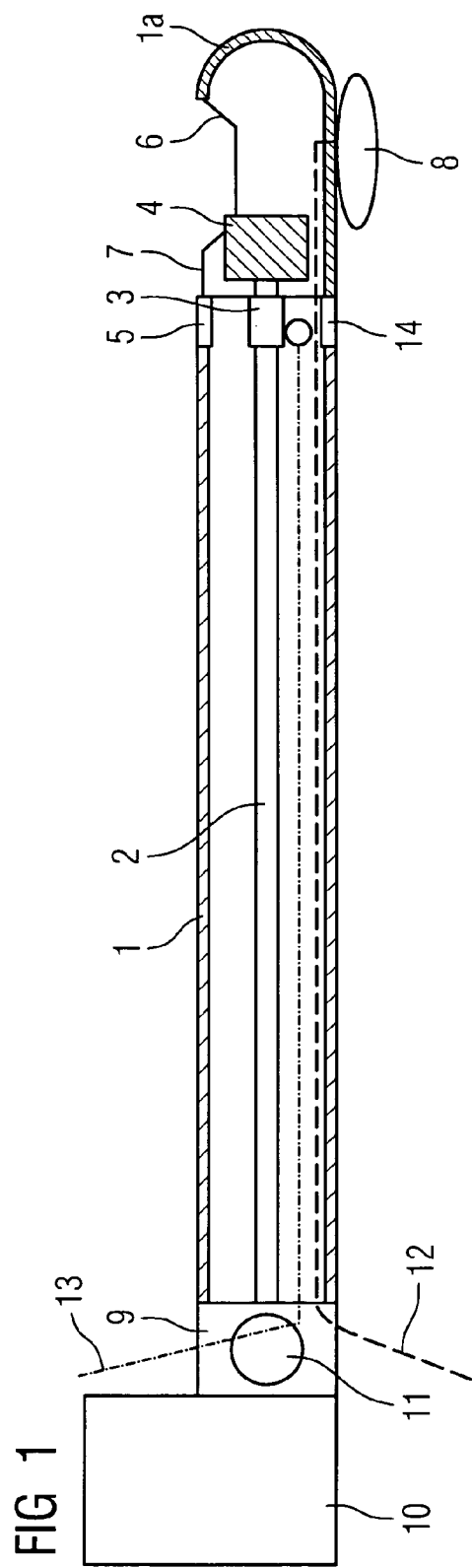
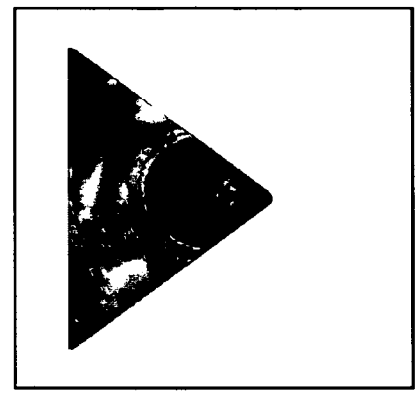
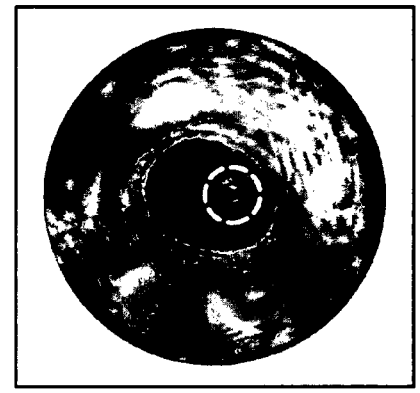

DEVICE FOR APPLYING AND MONITORING MEDICAL ATHERECTOMY

CROSS REFERENCE TO RELATED APPLICATIONS

This application claims priority to the German application No. 10 2004 008 371.1, filed Feb. 20, 2004 which is incorporated by reference herein in its entirety.

FIELD OF INVENTION

The invention relates to a device for carrying out and monitoring an atherectomy, with which a cutting knife driven in a rotating manner by an external unit set back to project into an opening in the tip of the catheter can be pressed onto the artery wall by means of an inflatable balloon arranged on the side of the catheter casing opposite the window opening.

BACKGROUND OF INVENTION

One of the most common fatal diseases is vascular disease, in particular cardiac infarct. This is caused by disease of the coronary arteries (arteriosclerosis). With this disease deposits (arteriosclerotic plaque) cause a "blockage" of the coronary arteries.

If coronary angiography shows serious narrowing (stenosis) of the coronary arteries, which causes angina pectoris, restricts performance and/or threatens the patient, in the majority of cases today a PTCA (Percutaneous Transluminal Coronary Angioplasty) is carried out. To this end the constrictions in the coronary arteries are widened using a so-called "balloon catheter".

Clinical studies have shown that with this method many patients suffer restenosis, with up to 50% of patients showing some degree of restenosis. The use of stents, which are inserted into the widened constriction, can reduce the restenosis rate by up to 25%.

DCA (Directional Coronary Atherectomy) is available to reduce restenosis further. DCA or "debulking" is a method for reopening stenosed coronary arteries.

The directional atherectomy device is a catheter system with a metal housing, in which the actual cutter is located. The cutter, which comprises a conically ground knife, is connected via a flexible connection to a motor outside the patient. The cutting knife is driven by this motor at a speed of 1500-2000 rpm. A balloon is mounted on one side of the metal housing and there is a window on the contralateral side. During the atherectomy the balloon is inflated and the openings and the knife are thereby pressed into the plaque. The rotating knife can now be pushed forward from outside towards the tip of the atherectomy housing. This causes the plaque to be cut out and the plaque material to be pushed into the tip of the atherectomy device. The balloon is then deflated, the atherectomy device rotated briefly, so that the window points towards another area of plaque and the process is repeated. [Interventional cardiology, angiology and cardiovascular surgery, Prof. V. Hombach, Schattauer Verlag Stuttgart, pages 111-115]

A device for DCA is for example disclosed in U.S. Pat. No. 5,895,402. The product Artherocath GTO from Guidant is known.

SUMMARY OF INVENTION

The therapy described above is carried out subject to X-ray control using contrast agents with an angiography device. The disadvantage of this method is that the coronary arteries are only shown in two dimensions and only the actual constriction is shown in the X-ray image. During the intervention the medical personnel are unable to distinguish between plaque and artery wall. This involves a significant risk for the patient as either too little plaque is removed and the required blood flow is not restored and the risk of restenosis remains or too much tissue is removed and this can result in perforation of the artery.

Clinical studies with the insertion of an IVUS (intravascular ultrasound) catheter into the artery improve the imaging information but have the disadvantage that a relatively expensive catheter also has to be inserted into the patient. Also the local resolution of IVUS is not particularly good. An IVUS system is disclosed for example in DE 198 27 460 A1 and in U.S. Pat. No. 5,193,546.

In U.S. Pat. No. 5,865,748 a device is disclosed, which combines an atherectomy device with an IVUS probe but this solution also has the disadvantage of the poor local resolution of IVUS. The artery wall is easier to identify but it is not possible to show the plaque with high resolution in the close-up range. A further disadvantage is the wave propagation of the ultrasound in the metal tip of the atherectomy catheter, which only allows compromises in the design of the catheter tip. Thus for example in U.S. Pat. No. 5,865,748 the metal tip is provided with holes to identify the position (encoder) of the ultrasound sensor, to obtain a longitudinal orientation. There is however a risk of plaque that has been removed escaping from these holes and causing a thrombosis.

An object of the invention is therefore to create a device to carry out the atherectomy, which allows simultaneous observation of the area of the intervention and also high resolution.

To achieve this object, the invention provides for an atherectomy catheter to be connected to an OCT catheter to form an integrated unit.

This results in an optimum system for debulking coronary arteries with the major advantage that it reduces both the number of method steps and the number of catheters used. Also the X-ray radiation required during the intervention is significantly reduced. The images of the OCT (Optical Coherence Tomography) system provide important additional medical information about the plaque and the artery wall, e.g. inflammatory processes. The "blocked" section of the artery can be identified and the elimination of the plaque can be controlled during and after the procedure. A further advantage of OCT is the very high detail resolution of structures close to the surface of the artery so that some microscopic tissue images can be displayed.

In a development of the invention there can also be provision for the rotating OCT signal lines—which are preferably arranged within a hollow flexible drive shaft for the OCT probe (rotatable mirror)—to be arranged inside the catheter casing of the atherectomy catheter, running from an external drive and evaluation unit to the OCT probe arranged within a ring-shaped window in the catheter casing directly in front of or behind the cutting knife.

A quite particularly advantageous embodiment of a device according to the invention results when the drive shaft for the OCT probe is also used to drive the cutting knife, with the option advantageously of a micro-transmission system being connected in front of the cutting knife, if necessary with a slip coupling.

The catheter casing, which can be provided with X-ray markers in a manner known per se, can advantageously be provided with inlet or outlet openings for contrast agents or rinsing fluid, as such a rinsing solution (e.g. physiological saline solution) has to be injected in the region of the site to be examined for the operation of the OCT catheter.

As well as the arrangement of magnets at the tip of the catheter for the purposes of magnetic navigation, the device can also be configured with a guide wire running through it.

BRIEF DESCRIPTION OF THE DRAWINGS

Further advantages, features and details of the invention will emerge from the description which follows of an exemplary embodiment and from the drawing, in which:

FIG. 1 shows a schematic sectional diagram of a combined atherectomy-OCT catheter according to the invention, FIG. 2 shows an OCT image from the artery with high resolution in the close-up range at the level of the transparent ring-shaped window and FIG. 3 shows an OCT image from the artery at the level of the metal tip of the catheter in the region of the window opening for the cutting knife.

DETAILED DESCRIPTION OF INVENTION

FIG. 1 shows a schematic diagram of a combined atherectomy-OCT catheter with an external flexible catheter casing 1 with a rigid catheter tip 1a. A hollow flexible drive shaft 2 with a glass-fiber line (not shown) running through it as the OCT line is arranged within the catheter casing. The hollow flexible drive shaft 2 serves both to drive a rotatable mirror forming the OCT sensor 3, which in the exemplary embodiment shown—viewed from the external end of the catheter out—is in front of the knife 4. The OCT sensor 3 lies within a revolving ring-shaped window 5, while the rotating knife 4 also driven by the drive shaft 2 passing through it projects into the window opening 6 of the rigid catheter tip 1a. The knife with its blade is therefore somewhat set back compared with the external contour 7 of the catheter tip 1a.

An inflatable balloon 8 on the side of the catheter tip 1a opposite the window opening 6 can press said catheter tip onto the inner wall of the artery, so that a region with plaque is pressed into the window opening and can thus be accessed and shaved off by the blade of the rotating cutting knife 4.

The mechanical connection system is marked 9, while the signal interface and drive unit are to be represented by 10. 11 indicates the schematic representation of the rotational coupling for the supply points and 12 a supply point for the pressure agent to inflate the balloon 8. Finally 13 indicates an inlet and 14 an outlet for contrast agents or rinsing fluid.

The combined catheter according to the invention is inserted subject to X-ray control, if necessary using contrast agents, into its target position (the stenosis), a guide wire also being used for insertion if necessary, said wire being inserted first into the artery, so that it can then feed in the catheter threaded onto the guide wire. An arrangement of magnets in the tip of the catheter can also be used for magnetic navigation if necessary. Once the required target position is reached, the rinsing fluid for the OCT method is injected and the stenosis is examined at high resolution using the OCT method. The tip of the catheter is then moved to the required position and held there with the balloon, if necessary with the additional aid of the angiography images. When a specific quantity of plaque has finally been removed, the OCT sensor is used once again to check the site on the artery wall and this process is repeated, until the plaque has been removed from all sites.

The invention is not restricted to the exemplary embodiment shown. As well as the possible extensions already addressed with regard to threading and navigation, it would also be possible particularly to insert a micro-transmission system into the drive shaft between the OCT sensor and the cutting knife with or without a slip coupling, to allow different rotation speeds for the OCT sensor and the cutting knife. It would also be possible to arrange the OCT sensor in a manner that is different from the arrangement shown distal to the cutter, i.e. right at the front of the catheter tip.

The invention claimed is:

1. A catheter device for performing and monitoring medical atherectomy, comprising:
    an atherectomy catheter assembly including a single external elongate casing having first and second opposing ends with a catheter tip at the first end, an inlet for receiving contrast agent or rinsing fluid near the second end and an outlet for discharging contrast agent or rinsing fluid and a rotatable cutting knife positioned between the first end and the inlet, the casing including an opening in a wall portion thereof through which the catheter tip projects;
    an inflatable balloon operatively positionable along the casing to press the cutting knife against a vascular wall;
    an OCT sensor comprising a rotatable mirror positioned in the casing between the first and second casing ends, with the casing including a ring-shaped window positioned about the sensor;
    a flexible drive assembly including a hollow shaft extending between the first and second ends and operatively coupled to simultaneously rotate both the mirror and the knife;
    an external OCT signaling line drive and evaluation unit coupled to the catheter assembly at the second end and connectable to drive said OCT sensor, wherein a fiber signaling line is positionable in the hollow flexible drive shaft to effect operative coupling of said unit to the OCT sensor, wherein configuration of the knife, the sensor, the hollow shaft, the unit and the balloon about the single casing enable provision of one catheter capable of providing both OCT images and atherectomy along the vascular wall.

2. The device according to claim 1, wherein the OCT sensor is arranged in front of or behind the knife.

3. The device according to claim 1, further comprising a micro gear unit connecting the drive shaft to the knife and arranged upstream the knife.

4. The device according to claim 3, wherein the micro gear unit has a slip clutch.

5. The device according to claim 1, further comprising a plurality of magnets arranged at the catheter tip for magnetically navigating the catheter assembly.

6. The device according to claim 1, further comprising a plurality of X-ray markers arranged on a catheter shaft of the catheter assembly.

7. The device according to claim 1,
    wherein the catheter assembly is placed about a target position and is configured to inject fluid to permit examination of a stenosis about the target position,
    wherein the OCT sensor is configured to provide first images received through the window positioned about the sensor for examining the stenosis,
    wherein the inflatable balloon is configured to hold the catheter tip in a desired position operatively positioned along the casing to press the cutting knife against a vascular wall,
    wherein the cutting knife is configured to remove plaque from the target position based on the first images, and
    wherein the OCT sensor is configured to provide second images after removal of the plaque.

* * * * *